(12) United States Patent
Lui et al.

(10) Patent No.: US 8,188,319 B2
(45) Date of Patent: May 29, 2012

(54) PROCESS FOR PREPARING 2,2-DIFLUOROETHYLAMINE

(75) Inventors: Norbert Lui, Odenthal (DE); Sergii Pazenok, Solingen (DE); Yuriy Grigorievich Shermolovich, Kiew (UA)

(73) Assignee: Bayer CropScience AG, Monheim (DE)

( * ) Notice: Subject to any disclaimer, the term of this patent is extended or adjusted under 35 U.S.C. 154(b) by 135 days.

(21) Appl. No.: 12/844,406

(22) Filed: Jul. 27, 2010

(65) Prior Publication Data

US 2011/0060167 A1 Mar. 10, 2011

Related U.S. Application Data

(60) Provisional application No. 61/229,051, filed on Jul. 28, 2009.

(30) Foreign Application Priority Data

Jul. 28, 2009 (EP) .................................... 09166574

(51) Int. Cl.
C07C 209/08 (2006.01)
(52) U.S. Cl. ........................................ 564/481; 564/482
(58) Field of Classification Search .................. 564/481, 564/482
See application file for complete search history.

(56) References Cited

U.S. PATENT DOCUMENTS 4,030,994 A 6/1977 Kollonitsch
4,618,718 A * 10/1986 Elliott et al. .................. 564/481
6,534,683 B2 * 3/2003 Takagi et al. .................. 564/481

OTHER PUBLICATIONS

Dickey, J. B., et al., "Fluorinated Aminoanthraquinone Dyes," *Industrial and Engineering Chemistry* 48(2):209-213, Tennessee Academy of Science, United States (1956).
Donetti, A., et al., "N-(Fluoroethyl)(imidazolylphenyl)formamidines. The Use of the Active Species of Mifentidine," *J. Med. Chem.* 32:957-961, American Chemical Society, United States (1989).
Houben-Weyl, "Intramolecular Dehydrohalo and Dehalogenation Reactions: B. Synthesis of Fluorinated Compounds," vol. E10 b/2, pp. 92-98, (2000).
Hudlicky, M., "Chemistry of Organic Fluorine Compounds," Ellis Horwood Limited, $2^{nd}$ Edition, pp. 489-490, United Kingdom (1976).
Kluger, R. & Chin, J., "Carboxylic Acid Participation in Amide Hydrolysis Evidence That Separation of a Nonbonded Complex Can Be Rate Determining," *J. Am. Chem. Soc.* 104:2891-2897, American Chemical Society, United States (1982).
Swarts, "Über einige fluorhaltige Alkylami," *Chem. Zentralbl.* 75:944-945 (1904).
Verniest, G., et al., "Synthesis and Reactivity of 1-Substituted 2-Fluoro- and 2,2-Difluoroaziridines," *J. Org. Chem.* 72:8569-8572, American Chemical Society, United States (2007).
International Search Report for International Application No. PCT/EP/2010/004434, European Patent Office, The Netherlands, mailed on Sep. 30, 2010.

* cited by examiner

*Primary Examiner* — Brian J Davis
(74) *Attorney, Agent, or Firm* — Sterne, Kessler, Goldstein & Fox, P.L.L.C.

(57) ABSTRACT

The present invention relates to a process for preparing 2,2-difluoroethylamine proceeding from 2,2-difluoro-1-haloethane using ammonia in a solvent which has a maximum water content of 15% by volume and in the presence of a catalyst which accelerates the reaction with ammonia.

8 Claims, No Drawings

PROCESS FOR PREPARING 2,2-DIFLUOROETHYLAMINE

The present invention relates to a process for preparing 2,2-difluoroethylamine proceeding from 2,2-difluoro-1-haloethane.

2,2-Difluoroethylamine is an important intermediate in active ingredient preparation. Various preparation methods for 2,2-difluoroethylamine are known.

Donetti et al. (J. Med. Chem. 1989, 32, 957-961) describe the synthesis of 2,2-difluoroethylamine hydrochloride proceeding from 2,2-difluoroacetamide. In this case, the desired amine is prepared with a diborane solution in tetrahydrofuran (THF). The yield is 48%.

Kluger et al. (JACS 1982, 104, 10, 2891-2897) describe the synthesis of 2,2-difluoroethylamine proceeding from amide with sodium boranate and boron trifluoride etherate. The yield is 60%.

Kollonitsch (U.S. Pat. No. 4,030,994) also describes a synthesis of 2,2-difluoroethylamine, namely the reaction of ethylamine with fluorooxytrifluoromethane in hydrogen fluoride under UV irradiation.

Swarts describes, in his article with the title "Über einige fluorhaltige Alkylamine" [Some fluorinated alkylamines] (Chem. Zentralblatt, volume 75, 1904, pages 944-945), the preparation of 2,2-difluoroethylamine and tetrafluoroethylamine, with subsequent removal of the two products by fractional distillation or by conversion thereof to chlorohydrates or oxalates. Swarts uses 1-bromo-2,2-difluoroethane and heats it to 125-145° C. in a tube with 2 mol of alcoholic ammonia for 3 days. Swarts describes the complete conversion of the starting compound to the compounds difluoroethylamine and tetrafluoroethylamine.

The preparation of 2,2-difluoroethylamine is also described in Dickey et al. (Industrial and Engineering Chemistry 1956, 2, 209-213). 2,2-Difluoro-1-chloroethane is reacted therein with 28% ammonium hydroxide, i.e. 28% aqueous ammonia solution, in a rocking autoclave. The reaction mixture is heated to temperatures of 135° to 140° C. for 31 hours. After the reaction has ended, the reaction mixture is filtered and the amine is distilled out of the reaction mixture. Since, however, there is still a lot of ammonia and some water in the distillate, the amine is dried over sodium hydroxide and distilled once again. The amine was thus obtained in a yield of 65%.

This process is disadvantageous since it requires—just like the Swarts process—a very long reaction time of 31 hours, and the yield of 65% is rather low. At the same time, the reaction mixture is highly corrosive since the aqueous ammonia in combination with the chloride and fluoride ions present in the reaction mixture attacks metallic materials at the high temperatures used in the process.

All these known processes are disadvantageous, especially because they cannot be performed on the economically viable industrial scale. The low yield and the use of expensive and hazardous chemicals, for example sodium boranate/$BF_3$ or diborane, prevent suitability of the processes according to Donetti et al. and Kluger et al. for the industrial scale preparation of 2,2-difluoroethylamine. The process according to Kollonitsch et al. uses hazardous chemicals, and pure 2,2-difluoroethylamine is not obtained. The process according to Dickey et. al. and the process according to Swarts are likewise unsuitable or uneconomic for use on the industrial scale, since they require very long reaction times and are at the same time not selective, and so the yields of the processes are unsatisfactory.

Proceeding from the known processes for preparing 2,2-difluoroethylamine, the problem is how 2,2-difluoroethylamine can be prepared in a simple and inexpensive manner. Inexpensive processes are understood to mean those processes which can be performed without a great financial investment, because the starting materials, for example, are nonhazardous, no other technical problems occur, for example because the reaction mixture is corrosive, and/or the desired 2,2-difluoroethylamine is obtained in a sufficiently high yield and purity, for instance because the reaction proceeds substantially selectively.

Proceeding from 2,2-difluoro-1-haloethane, a process has now been found for preparing 2,2-difluoroethylamine which is performable simply and inexpensively, especially because the 2,2-difluoro-1-haloethane starting material reacts even under comparatively mild reaction conditions and with short reaction times selectively to give the desired 2,2-difluoroethylamine.

The invention therefore provides a process for preparing 2,2-difluoroethylamine, comprising the reaction of 2,2-difluoro-1-haloethane having the following general formula (I):

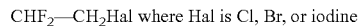

$CHF_2$—$CH_2Hal$ where Hal is Cl, Br, or iodine with $NH_3$ (ammonia) in a solvent which has a maximum water content of 15% by volume and in the presence of a catalyst which accelerates the reaction with ammonia, optionally with subsequent purification, preferably distillative purification. 2,2-Difluoro-1-haloethane of the general formula (I) in which Hal is chlorine and bromine is preferred. The compound $CHF_2$—$CH_2Cl$ (2,2-difluoro-1-chloroethane) is very preferred.

The molar ratio of 2,2-difluoro-1-haloethane to the ammonia $NH_3$ used is in the range from about 0.8:1 to about 1:30, preferably in the range from about 1:2 to about 1:20, more preferably in the range from about 1:3 to about 1:12.

According to the invention, solvents which have a maximum water content of 15% by volume are used. Preference is given to solvents which have a maximum water content of 5% by volume, more preferably of not more than 2.5% by volume and most preferably of not more than 0.5% by volume.

Solvents are generally used in such an amount that the reaction mixture is efficiently stirrable over the entire process. Advantageously, based on the 2,2-difluoro-1-haloethane used, 1 to 50 times the amount of solvent, preferably 2 to 40 times the amount of solvent, more preferably 2 to 20 times the amount of solvent, is used.

Useful solvents for performing the process according to the invention include all organic solvents which are inert under the reaction conditions. According to the invention, solvents are also understood to mean mixtures of pure solvents.

Solvents suitable in accordance with the invention are especially alcohols (e.g. methanol, ethanol, isopropanol, butanol (i.e. n-butanol, tert-butanol, 2-butanol), 2-(2-ethoxyethoxy)ethanol, diethylene glycol); ethers (e.g. ethyl propyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzylmethyl sulphoxide, diisobutyl sulphoxide, dibutyl sulphoxide, diisoamyl sulphoxide; sulphones such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons (e.g. pentane, hexane, heptane, octane, nonane, such as the "white spirits" with components having boiling points in the range, for example, from 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, xylene); esters (e.g. methyl acetate, ethyl acetate, butyl acetate, isobutyl acetate, dimethyl carbonate, dibutyl carbonate or ethylene carbonate, propylene carbonate); amides (e.g. hexamethylenephosphoramide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolindione, N-formylpiperidine, N,N'-1,4-diformylpiperazine) or mixtures thereof.

In the process according to the invention, the solvents used are preferably alcohols, especially n-butanol, amides, especially N-methylpyrrolidine or 1,3-dimethyl-2-imidazolindione, ethers, especially triethylene glycol dimethyl ether, and also dimethyl sulphoxide or tetramethylene sulphoxide, or mixtures thereof.

Suitable catalysts for use in the process according to the invention are all of those which accelerate the reaction with ammonia. Mixtures of suitable catalysts are also conceivable. Suitable catalysts in accordance with the invention are especially alkali metal bromides and iodides (e.g. sodium iodide, potassium iodide, potassium bromide); ammonium bromide and ammonium iodide; tetraalkylammonium bromides and iodides (e.g. tetraethylammonium iodide); particular phosphonium halides such as tetraalkyl- or tetraarylphosphonium halides (e.g. hexadecyltributylphosphonium bromide, stearyltributylphosphonium bromide, tetrabutylphosphonium bromide, tetraoctylphosphonium bromide, tetraphenylphosphonium chloride and tetraphenylphosphonium bromide), tetrakis(dimethylamino)phosphonium bromide, tetrakis-(diethylamino)phosphonium bromide, tetrakis (dipropylamino)phosphonium chloride and tetrakis(dipropylamino)phosphonium chloride bromide; and bis(dimethylamino)[(1,3-dimethyl-imidazolidin-2-ylidene)amino]methyl bromide.

In the process according to the invention, the catalysts used are preferably sodium iodide, potassium iodide, tetrabutylammonium bromide or tetraphenylphosphonium bromide, more preferably sodium iodide or potassium iodide.

The catalyst can also be generated in situ, for example by a reaction of HBr or HI with ammonia.

In addition, the catalyst can also be generated in situ by addition of very reactive alkyl bromides or iodides (e.g. methyl bromide, methyl iodide, ethyl bromide or ethyl iodide).

In the process according to the invention, the catalyst, based on the 2,2-difluoro-1-haloethane used, is used in a concentration of about 0.01 to about 25% by weight. Higher concentrations are possible in principle. Preference is given to using the catalyst in a concentration of about 0.2 to about 25% by weight, more preferably of about 0.4 to about 20% by weight, most preferably of about 0.5 to about 15% by weight.

The catalyst can, however, also be used preferably in a concentration of about 0.05 to about 3% by weight, of about 0.1 to about 10% by weight or of about 0.5 to about 10% by weight.

The inventors have determined that the selectivity and hence the yield, and also the reaction rate of the conversion, are very advantageous as a result of the use of a catalyst which accelerates the reaction with ammonia and as a result of the use of solvent with a maximum water content of 15% by volume, and form the basis of the fact that the reaction can be performed on the industrial scale.

The reaction mixture is also less corrosive as a result of the use of a solvent with a maximum water content of 15% by volume, because fewer fluorine or halogen ions are eliminated from the 2,2-difluoro-1-haloethane.

The inventive reaction can be performed within a wide temperature range (for example in the range from about 50° C. to about 200° C.). Preference is given to performing the reaction within a temperature range from about 80° C. to about 160° C.

The reaction is in principle performed under autogenous pressure in a pressure-stable closed experimental vessel (autoclave). The pressure during the reaction (i.e. the autogenous pressure) depends on the reaction temperature used, the solvent used, the 2,2-difluoro-1-haloethane used and the amount of ammonia used. When a pressure increase is desired, an additional pressure increase can be performed by means of addition of an inert gas, such as nitrogen or argon.

The reaction time of the reaction is short and is within the range from about 0.5 to about 10 hours. A longer reaction time is possible but economically unviable.

As already mentioned, the desired 2,2-difluoroethylamine is obtained by the process according to the invention with good yields, short reaction times and in high purity, such that an extensive workup of the direct reaction product is generally not required. All of this is surprising, since M. Hudlicky, Chemistry of Organofluorine Compounds, 2nd Edition, 1976, p. 489-490 and Houben Weyl, E 10b/2 p. 92-98 disclose that the vinylidene fluoride forms preferentially under basic conditions, and can form with elimination of HCl, HBr or HI from 2,2-difluorohaloethane. J. Org. Chem. 2007, 72 (22) 8569 also discloses that 2,2-difluoroethylamine is very reactive and can react further under the inventive reaction conditions.

The reaction mixture can be worked up and purified via 2,2-difluoroethylamine or via the salts thereof. Normally, the unconverted ammonia is recovered, preferably by distillation, and any ammonium salts present are filtered off. The 2,2-difluoroethylamine can then be isolated from the reaction mixture under standard pressure or under reduced pressure, preferably by distillation.

A 2,2-difluoroethylamine salt, for example salts of organic or inorganic acids (e.g. hydrochlorides or acetates), are purified preferably by crystallization. 2,2-Difluoroethylamine salts are, for example, 2,2-difluoroethylamine hydrochloride or 2,2-difluoroethylamine acetate. Water-soluble salts can be purified by extraction of the aqueous solutions. The amine can then finally be released from its salts by reaction with organic or inorganic bases. Preferred bases are $NaHCO_3$, $Na_2CO_3$ or NaOH.

The present invention is illustrated in detail by the examples which follow, without restricting the invention thereto.

PREPARATION EXAMPLES

Example 1

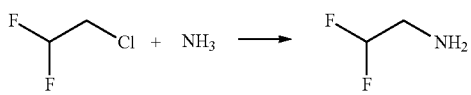

An autoclave is initially charged with 15 g (0.149 mol) of 2,2-difluoro-1-chloroethane, 1.5 g of potassium iodide and 30 g of N-methylpyrrolidine having a water content of 100 ppm, i.e. 0.01% by volume, and 20.2 g of ammonia are added. The molar ratio of 2,2-difluoro-1-chloroethane to ammonia is 1:8. The reaction mixture is heated to 143°-145° C. and stirred at this temperature for 5.5 hours. The reaction mixture is cooled to 50° C. and the excess ammonia is distilled off. The precipitated ammonium salt is filtered off and washed with 5 g of N-methylpyrrolidine. The free difluoroethylamine is subsequently distilled out of the mother liquor and wash solution at 1-10 mbar. This gives 88% yield.

NMR $^1$H (CDCl$_3$): 5.5-5.9 (m, 1H), 2.94-3.1 (m, 2H), 1.26 (br m, NH$_2$)

Example 2

An autoclave is initially charged with 25 g (0.249 mol) of 2,2-difluoro-1-chloroethane, 2.5 g of potassium iodide and 250 g of dimethyl sulphoxide (DMSO) having a water content of 150 ppm, i.e. 0.015% by volume, and 25.4 g of ammonia are added. The molar ratio of 2,2-difluoro-1-chloroethane to ammonia is 1:6. The reaction mixture is heated to 143-145° C. and stirred at this temperature for 4.5 hours. The reaction mixture is cooled to 50° C. and the excess ammonia is distilled off. The difluoroethylamine is subsequently distilled out of the reaction mixture at 1-10 mbar. The distillate, which still contains small amounts of solvent, is then redistilled at standard pressure. This gives 87% yield.

Example 3

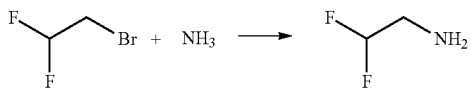

An autoclave is initially charged with 14.5 g (0.1 mol) of 2,2-difluoro-1-bromoethane, 0.5 g of potassium iodide and 50 g of DMSO having a water content of 250 ppm, i.e. 0.025% by volume, and 6.8 g of anhydrous ammonia are added. The molar ratio of 2,2-difluoro-1-bromoethane to ammonia is 1:4. The reaction mixture is heated to 100° C. and stirred at this temperature for 1 hour. The reaction mixture is cooled to 50° C. and the excess ammonia is distilled off. The difluoroethylamine is subsequently distilled out of the reaction mixture at 1-10 mbar. The distillate, which still contains small amounts of solvent, is then redistilled at standard pressure. This gives 82% yield.

Example 4

Procedure as Example 3. Instead of potassium iodide, 1 g of tetraethylammonium iodide is used. This gives 78% yield.

Example 5

An autoclave is initially charged with 14.5 g (0.1 mol) of 2,2-difluoro-1-bromoethane, 0.5 g of potassium iodide and 50 g of n-butanol having a water content of 250 ppm, i.e. 0.025% by volume, and 6.8 g of ammonia are added. The molar ratio of 2,2-difluoro-1-bromoethane to ammonia is 1:4. The reaction mixture is heated to 150° C. and stirred at this temperature for 2 hours. The reaction mixture is cooled to 50° C. and the excess ammonia is distilled off. The difluoroethylamine is subsequently distilled out of the reaction mixture at 1-10 mbar. The distillate, which still contains small amounts of solvent, is then redistilled at standard pressure. This gives 70% yield.

Comparative Example

An autoclave is initially charged with 14.5 g (0.1 mol) of 2,2-difluoro-1-bromoethane, 1 g of potassium iodide and 50 g of DMSO, and 27.5 g of a 25% aqueous ammonia solution are added. The reaction mixture is heated to 100° C. and stirred at this temperature for 1.2 hours. The reaction mixture is cooled to 50° C. and the excess ammonia is distilled off. The difluoroethylamine is subsequent distilled out of the reaction mixture at 1-10 mbar. The distillate, which still contains small amounts of solvent, is then redistilled at standard pressure. This gives 13% yield.

The invention claimed is:

1. Process for preparing 2,2-difluoroethylamine, wherein said process comprises reacting 2,2-difluoro-1-haloethane having the general formula (I):

where Hal is chlorine, bromine, or iodine with ammonia in a solvent which has a maximum water content of 15% by volume and in the presence of a catalyst which accelerates the reacting of 2,2-difluoro-1-haloethane with ammonia.

2. Process according to claim 1, wherein the molar ratio of 2,2-difluoro-1-haloethane to the ammonia used is in the range from 0.8:1 to 1:30.

3. Process according to claim 1, wherein the solvent is selected from methanol, ethanol, isopropanol, butanol, 2-(2-ethoxyethoxy)ethanol, diethylene glycol, ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropylethyl ether, diethylene glycol dimethyl ether, triethylene glycol dimethyl ether, tetrahydrofuran, dioxane, and polyethers of ethylene oxide and/or propylene oxide, hexamethylenephosphoramide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2 (1H)-pyrimidine, octylpyrrolidone, octylcaprolactam, 1,3-dimethyl-2-imidazolindione, N-formylpiperidine, N,N'-1,4-diformylpiperazine and dimethyl sulphoxide.

4. Process according to claim 1, wherein the catalyst is formed in situ.

5. Process according to claim 1, wherein the catalyst is selected from potassium bromide, sodium iodide, potassium iodide and tetrabutylammonium bromide.

6. Process according to claim 2, wherein the solvent is selected from methanol, ethanol, isopropanol, butanol, 2-(2-ethoxyethoxy)ethanol, diethylene glycol, ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropylethyl ether, diethylene glycol dimethyl ether, triethylene glycol dimethyl ether, tetrahydrofuran, dioxane, and polyethers of ethylene oxide and/or propylene oxide, hexamethylenephosphoramide, formamide, N,N-dimethylacetamide, N-methylformamide, N,N-dimethylformamide, N,N-dipropyl-formamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolindione, N-formylpiperidine, N,N'-1,4-diformylpiperazine and dimethyl sulphoxide.

7. Process according to claim 2, wherein the catalyst is formed in situ.

8. Process according to claim 2, wherein the catalyst is selected from potassium bromide, sodium iodide, potassium iodide and tetrabutylammonium bromide.

* * * * *